(12) United States Patent
Quarre et al.

(10) Patent No.: US 11,402,301 B2
(45) Date of Patent: Aug. 2, 2022

(54) DEVICE, SYSTEM, AND METHOD FOR SELECTING A TARGET ANALYTE

(71) Applicant: RareCyte, Inc., Seattle, WA (US)

(72) Inventors: Steve Quarre, Woodinville, WA (US); Ronald C. Seubert, Seattle, WA (US)

(73) Assignee: RareCyte, Inc., Seattle, WA (US)

(*) Notice: Subject to any disclaimer, the term of this patent is extended or adjusted under 35 U.S.C. 154(b) by 329 days.

(21) Appl. No.: 16/811,565

(22) Filed: Mar. 6, 2020

(65) Prior Publication Data
US 2020/0284698 A1 Sep. 10, 2020

Related U.S. Application Data

(60) Provisional application No. 62/815,903, filed on Mar. 8, 2019.

(51) Int. Cl.
*G01N 1/14* (2006.01)
*G01N 33/49* (2006.01)

(52) U.S. Cl.
CPC ............... *G01N 1/14* (2013.01); *G01N 33/49* (2013.01); *G01N 2001/1418* (2013.01)

(58) Field of Classification Search
CPC .. G01N 1/14; G01N 33/49; G01N 2001/1418; G01N 35/1009; G01N 2035/1037; B01L 3/021
See application file for complete search history.

(56) References Cited

U.S. PATENT DOCUMENTS

| | | | | |
|---|---|---|---|---|
| 5,525,302 A * | 6/1996 | Astle | ...................... | B01L 3/0279 422/522 |
| 6,702,990 B1 * | 3/2004 | Camacho | .............. | B01L 3/0275 83/167 |
| 9,227,188 B2 * | 1/2016 | Quarre | .................. | B01L 3/0275 |
| 2005/0016921 A1 * | 1/2005 | Gjerde | .................. | G01N 35/10 436/178 |
| 2008/0166441 A1 * | 7/2008 | Kintzinger | .......... | B29C 45/4225 425/185 |
| 2012/0213677 A1 * | 8/2012 | Petrek | ..................... | B01L 3/022 422/524 |
| 2017/0274570 A1 * | 9/2017 | Schad | ................. | B29C 45/7207 |

FOREIGN PATENT DOCUMENTS

WO WO-2012012779 A2 * 1/2012 .............. B01L 3/021

\* cited by examiner

*Primary Examiner* — Francis C Gray
(74) *Attorney, Agent, or Firm* — Shay Glenn LLP

(57) ABSTRACT

This disclosure is directed to a device and a system for picking a target material from a sample.

20 Claims, 16 Drawing Sheets

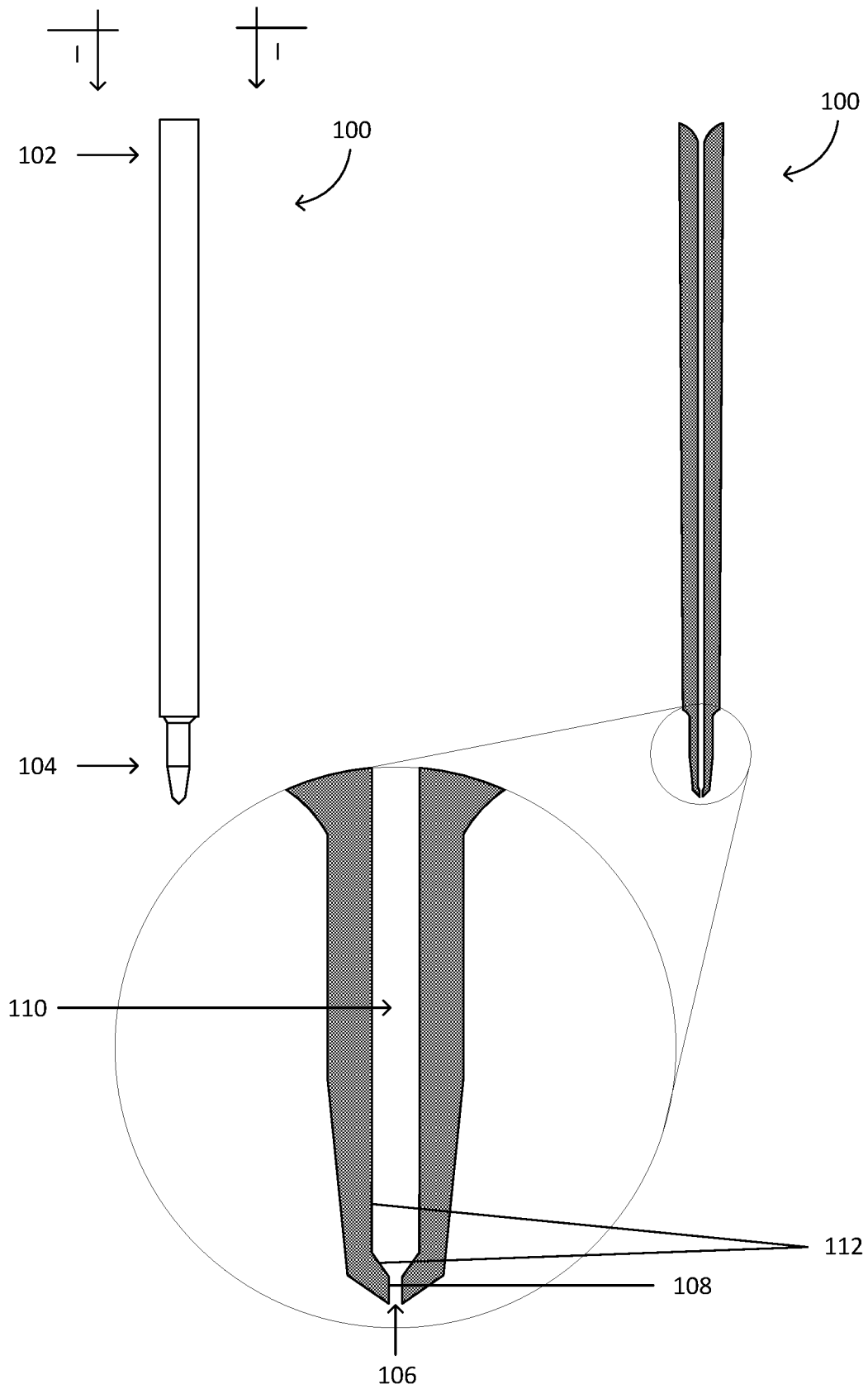

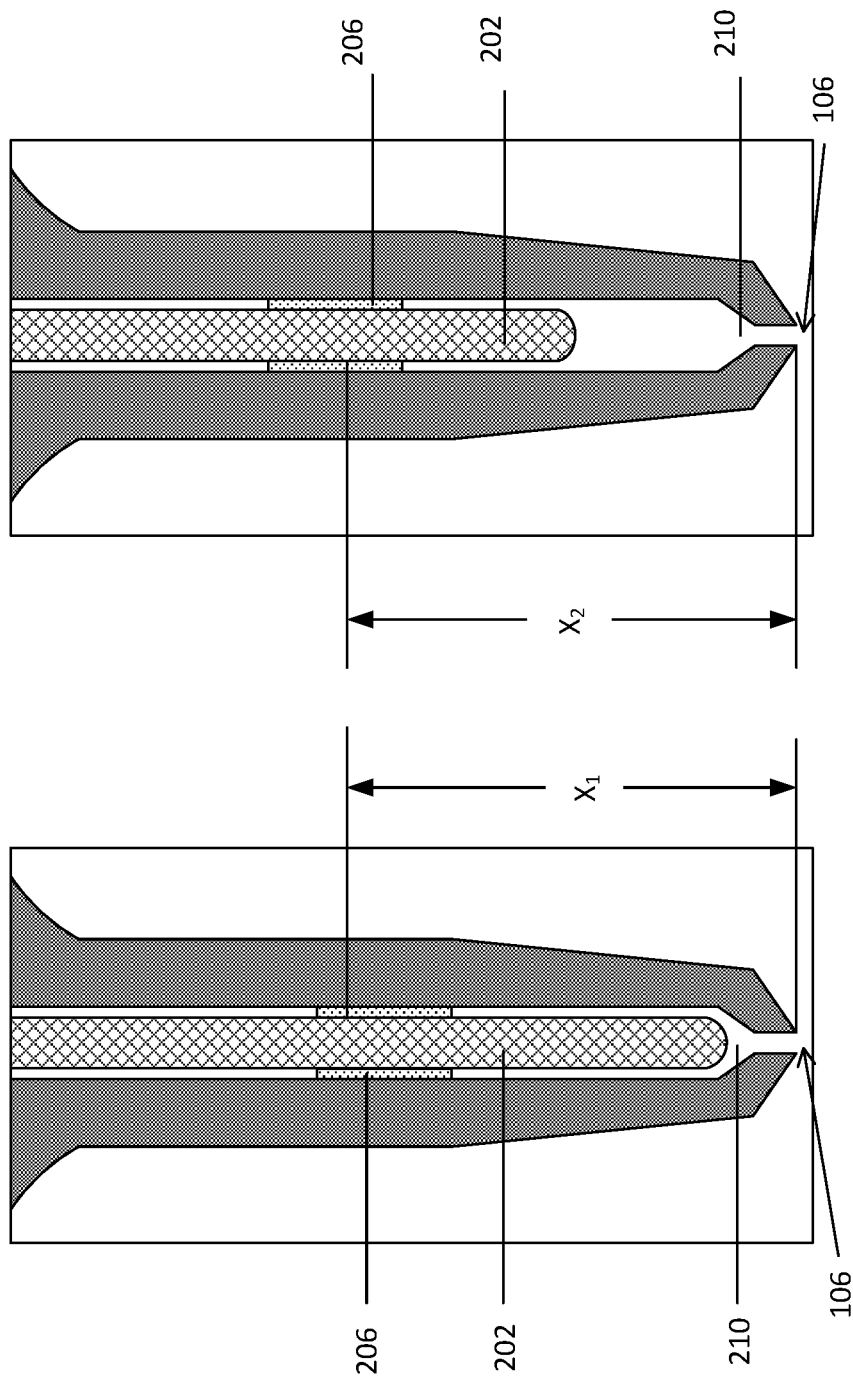

DEVICE, SYSTEM, AND METHOD FOR SELECTING A TARGET ANALYTE

CROSS REFERENCE TO RELATED APPLICATIONS

This application claims the benefit of Provisional Application No. 62/815,903, filed Mar. 8, 2019.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

This disclosure relates generally to micromanipulation of a target material, though more specifically, to picking and isolating the target material.

BACKGROUND

Samples often include materials of interest that are difficult to extract and isolate for analysis. As a result, practitioners, researchers, and those working with suspensions continue to seek systems and methods to more efficiently and accurately isolate and extract target materials from a sample.

SUMMARY OF THE DISCLOSURE

In a first aspect, a picker hear is provided. The picker head comprises a tip comprising a first end; a second end comprising an opening; and a bore extending from the first end to the opening. The picker head comprises a piston comprising a first end and a second end, wherein the second end is configured to be inserted into the bore; and a sealing fluid configured to at least partially fill the bore, wherein when the sealing fluid is within the bore the sealing fluid comprises a first side proximal to the first end of the tip and a second side proximal to the opening, wherein the sealing fluid is selected to satisfy the condition given by:

$$F_{DSF} > F_{DBS}$$

wherein $F_{DSF}$ represents a force required to displace the sealing fluid within the bore; and wherein $F_{DBS}$ represents a force required to displace a fluid or material within a portion of the bore extending from the second side of the sealing fluid to an external side of the opening.

In some embodiments, the force to displace the sealing fluid is a function of one or more of (1) at least one of the viscosity or surface tension of the sealing fluid; (2) a gap distance between an outer wall of the piston and an inner wall of the tip; (3) friction force of the outer wall of the piston; (4) friction force of the inner wall of the tip; or (5) a length of a portion of the bore extending from the first side of the sealing fluid to the second end of the tip. The sealing fluid can be a liquid. In some embodiments, the sealing fluid has a viscosity of approximately 0.2-80,000 mPa-s. The picker head can comprise a hydraulic fluid at least partially filling a portion of the bore between the second side of the sealing fluid and the opening. In some embodiments, at least one internal section of the bore is coated with a substance that attracts the hydraulic fluid. At least one section of the piston can be coated with a substance to repel the sealing fluid. In some embodiments, the sealing fluid and the hydraulic fluid are different liquids. The sealing fluid and the hydraulic fluid can be immiscible with each other. In some embodiments, the picker head comprises a gap between an inner wall of the tip and an outer wall of the piston having a clearance of approximately 0.01-100 μm. The sealing fluid can be further selected to satisfy the condition given by:

$$\Delta V_{sealing\ fluid} + \Delta V_{piston} + \Delta V_{bore\ segment} = 0$$

wherein $\Delta V_{sealing\ fluid}$ represents a change in volume of the sealing fluid within a pre-determined portion of the picker head when the piston is moved from a first state to a second state; wherein $\Delta V_{piston}$ represents a change in volume of the piston within the pre-determined portion of the picker head when the piston is moved from the first state to the second state; and wherein $\Delta V_{bore\ segment}$ represents a change in volume of a bore segment comprising any portion of the bore and the opening within the pre-determined portion of the picker head not occupied by the sealing fluid or the piston when the piston is moved from the first state to the second state. In some embodiments, the opening has a first diameter, wherein the piston has a second diameter, and wherein the ratio of the second diameter to the first diameter is greater than 1:1. The ratio can be greater than 1:1 and less than 2:1. The ration can be at least 1.9:1. The ratio can be at least 1.5:1. In some embodiments, the first diameter is 250 μm. The second diameter can be greater than 250 μm.

In another aspect, a picker is provided. The picker comprises a picker head comprising a tip comprising a first end; a second end comprising an opening; and a bore extending from the first end to the opening. The picker comprises a piston comprising a first end and a second end, wherein the second end is configured to be inserted into the bore; and a sealing fluid configured to at least partially fill the bore, wherein when the sealing fluid is within the bore the sealing fluid comprises a first side proximal to the first end of the tip and a second side proximal to the opening, wherein the sealing fluid is selected to satisfy the condition given by:

$$F_{DSF} > F_{DBS}$$

wherein $F_{DSF}$ represents a force required to displace the sealing fluid within the bore; and wherein $F_{DBS}$ represents a force required to displace a fluid or material within a portion of the bore extending from the second side of the sealing fluid to an external side of the opening.

In some embodiments, the picker comprises a driver; and a gripper mating the driver to the piston. The picker can comprise a mount connecting the driver, the gripper, and the picker head to an imaging or detection device.

BRIEF DESCRIPTION OF THE DRAWINGS

FIG. 1A shows an example tip.
FIG. 1B shows a cross-section of the example tip.
FIGS. 2A-2F show an example picker head.

DETAILED DESCRIPTION

Figures 2A, 2B:
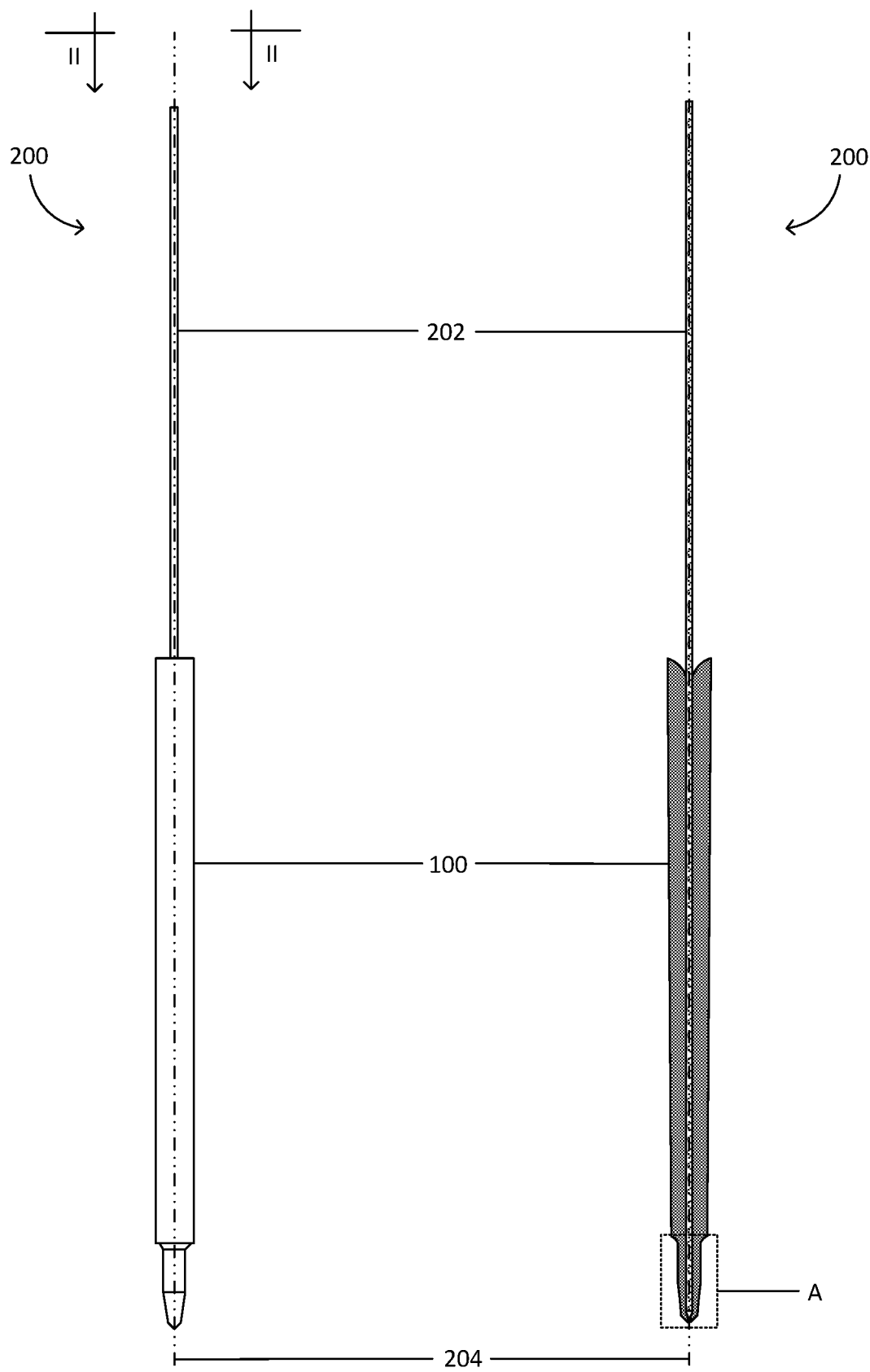

This disclosure is directed to a device and a system for picking a target material from a sample. In one embodiment, the device and system comprise a sealing fluid of mineral oil. In certain embodiments, the mineral oil may have a viscosity of approximately 0.2-80,000 mPa-s and approximately 0.3-73,000 mPa-s. More specifically, embodiments of the mineral oil have viscosities of approximately 2500-2600 mPa-s and approximately 7600-7700 mPa-s. Mineral oil, having viscosities of approximately 2500-2600 mPa-s and approximately 7600-7700 mPa-s, is used when a gap distance between a piston and a tip is approximately 0.0125-0.04 mm or approximately 0.0375-0.12 mm, respectively. In another embodiment, the sealing fluid is silicone grease. The silicone grease has a viscosity of approximately 0.2-80,000 mPa-s. More specifically, silicone grease can have a viscosity of approximately 900-1000 mPa-s. Silicone grease, having a viscosity of approximately 900-1000 mPa-s, is used when the gap distance is 0.0045-0.016 mm.

Suitable devices, systems, and/or methods for target analyte retrieval, isolation, or picking may include those described in one or more of the following U.S. patents and published applications, each of which is hereby incorporated by reference in its entirety: U.S. Pat. Nos. 9,222,953; 9,440,234; 9,519,002; 9,810,605; 10,088,392; 2017/0276575.

In the following description, the terms "fill" or "filled" are used to describe one entity or material being put into and/or occupying the volume of another entity or material. In one aspect, "fill" or "filled" can include the entire volume of one entity or material being occupied by the other entity or material. In another aspect, "fill" or "filled" can include less than the entire volume of one entity or material being occupied by the other entity or material.

Tip

FIG. 1A shows a tip 100. FIG. 1B shows a cross-section of the tip 100 taken along line I-I and a magnified view. The tip 100 comprises a first end 102 and a second end 104. The second end 104 comprises an opening 106 formed by a first inner wall 108. The tip 100 further comprises a bore 110, formed by a second inner wall 112, such that the bore 110 extends from the opening 106 to the first end 102 of the tip 100.

The opening 106 can have any appropriate shape (including cylindrical, rectangular, cubical, or the like) and any appropriate size (for example, at least 1 nm, at least 10 nm, at least 100 nm, at least 1 µm, at least 10 µm, at least 25 µm, at least 50 µm, at least 100 µm, at least 200 µm, at least 250 µm, at least 500 µm, at least 750 µm, at least 1 mm, and at least 1 cm; for example, 1 nm, 10 nm, 100 nm, 1 µm, 10 µm, 25 µm, 50 µm, 100 µm, 200 µm, 250 µm, 500 µm, 750 µm, 1 mm, and 1 cm; for example, 1 nm to 1 cm). An outer wall of the tip 100 proximal to the opening 106 can be sharpened, thereby having an angle from the horizontal that may range from 1° to 89°, including, without limitation 1° to 30°, 30° to 89°, 1°, 10°, 20°, 30°, 33°, 45°, 60°, 70°, 75°, 80°, or 89°.

The first inner wall 108 can be straight or tapered. In one embodiment, the second inner wall 112 is a single wall being straight or tapered. In one embodiment, the second inner wall 112 has varying slopes, tapers, and/or curves along its entirety. A suitable tip may include one described in U.S. Pat. No. 9,227,188, which is hereby incorporated by reference in its entirety.

When the bore 110 is tapered, a sleeve (not shown) can be provided to provide a straight hole to retain linearity (e.g., to maintain a consistent gap distance, and/or to ensure components are coaxial) between the components of the tip 100.

The tip 100 can be a single piece or composed of a plurality of pieces.

The tip 100 can be composed of a variety of different materials including, but not limited to, ceramics; glass; metals; silicon; organic or inorganic materials; plastic materials; polymers; jewels (i.e. ruby, sapphire, or diamond); combinations thereof; and the like. Furthermore, the tip 100 may be composed of a material that is fluorescent. In one embodiment, the tip 100 can be impact-resistant, hard, and dimensionally stable (i.e. axially and/or torsionally stiff).

Picker Head

Figure 2C:
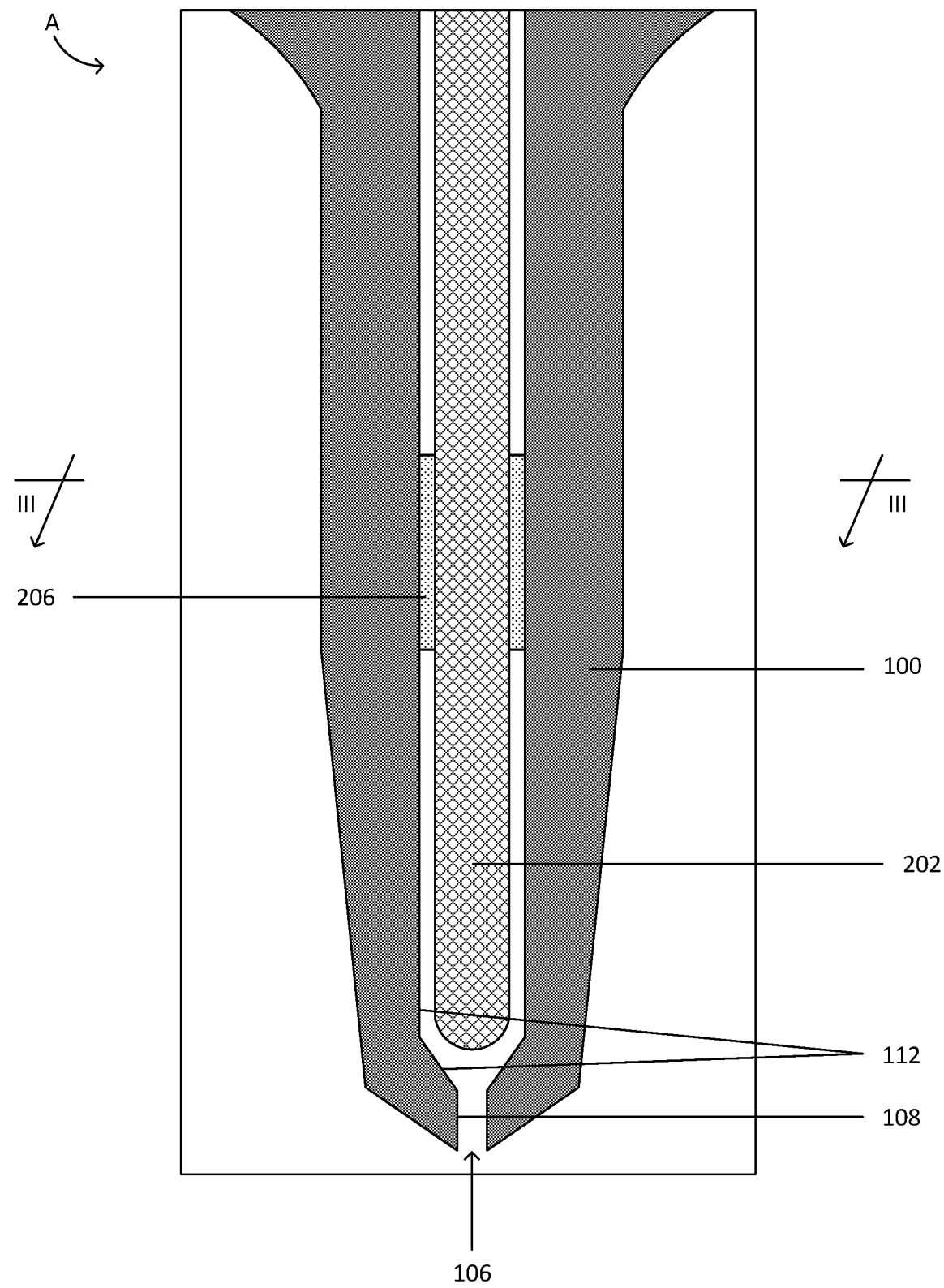
Figure 2D:
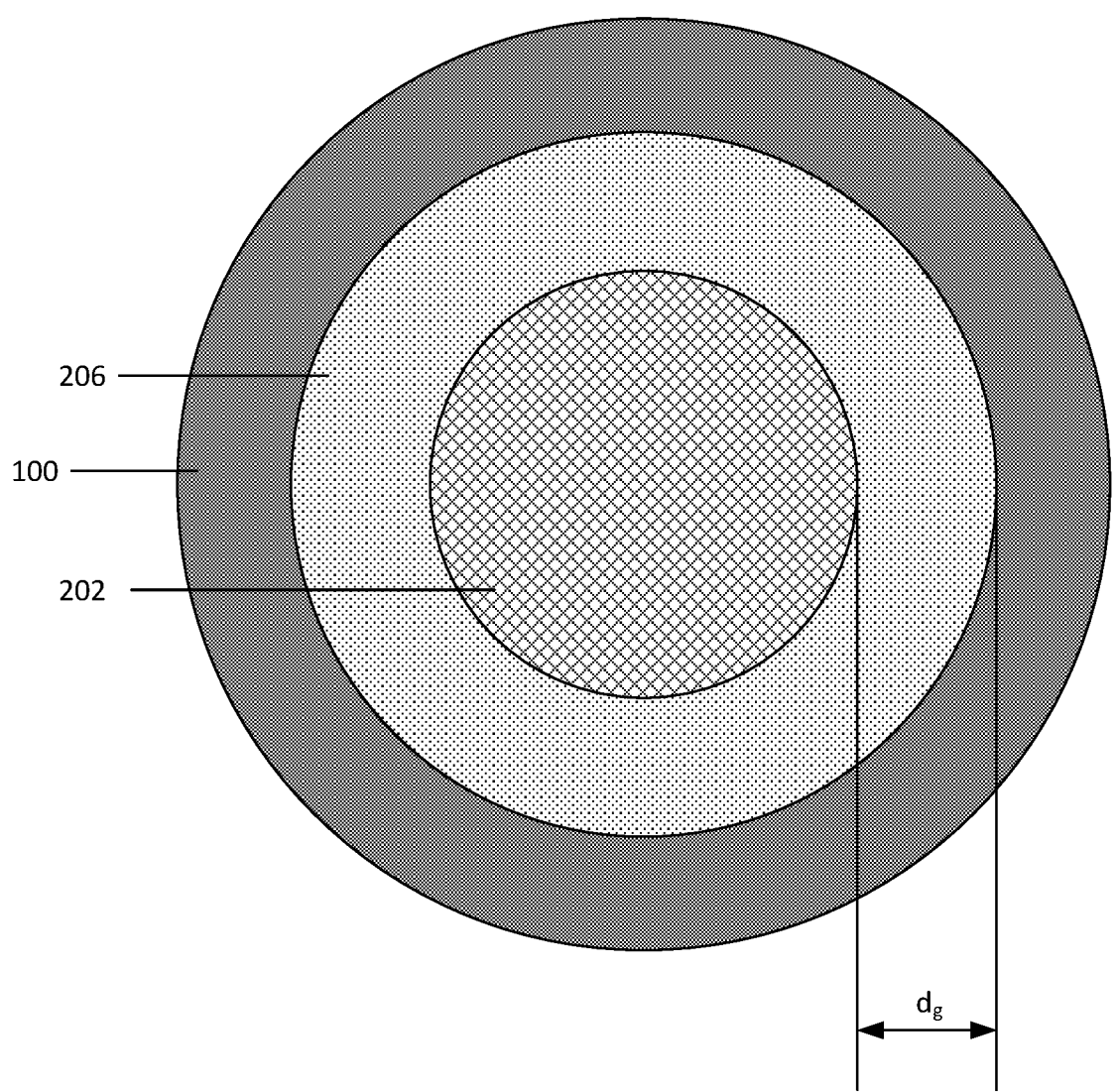

FIG. 2A shows a picker head 200. FIG. 2B shows a cross-section of the picker head 200 taken along line II-II. FIG. 2C shows an enlarged cross-section (A) of the picker head 200 as shown in FIGS. 2A-2B. FIG. 2D shows a cross-section of the picker head 200 taken along line III-III.

The picker head 200 comprises a piston 202, a sealing fluid 206, and the tip 100. The piston 202 comprises a first end, a second end, and a main body extending between the first and second ends. The second end of the piston 202 extends into the tip 100. The tip 100 allows for translation of the piston 202, for example, along the axis 204. The piston 202 can also be rotated (i.e. clockwise or counter-clockwise) about the axis 204, if it is desirous or advantageous to do so.

The second end of the piston 202 can be appropriately shaped, including, for example, cylindrical, semi-spherical, pyramidal, cubical, shaped to match the second inner wall 112, or the like. The second end of the piston 202 can have any appropriate shape (including cylindrical, rectangular, cubical, or the like) and any appropriate size (for example, at least 1 nm, at least 10 nm, at least 100 nm, at least 1 µm, at least 10 µm, at least 25 µm, at least 50 µm, at least 100 µm, at least 200 µm, at least 250 µm, at least 500 µm, at least 750 µm, at least 1 mm, and at least 1 cm; for example, 1 nm, 10 nm, 100 nm, 1 µm, 10 µm, 25 µm, 50 µm, 100 µm, 200 µm, 250 µm, 500 µm, 750 µm, 1 mm, and 1 cm; for example, 1 nm to 1 cm; for example, greater than 1 nm, greater than 10 nm, greater than 100 nm, greater than 1 µm, greater than 10 µm, greater than 25 µm, greater than 50 µm, greater than 100 µm, greater than 200 µm, greater than 250 µm, greater than 500 µm, greater than 750 µm, greater than 1 mm, and greater than 1 cm). The second end of the piston 202 can be smaller than, equal to, or greater than the size of the opening 106.

In one embodiment, one of the first or second ends of the piston 202 can be enlarged, thereby having a diameter greater than the diameter of the other end and/or the main body. The ratio of piston 202 size to opening 106 size is greater than 1:1 (for example, 1.01:1, 1.1:1, 1.25:1, 1.5:1, 1.75:1, 1.8:1, 1.9:1, 2:1, and 3:1; for example, 1.01:1, at least 1.1:1, at least 1.25:1, at least 1.5:1, at least 1.75:1, at least 1.8:1, at least 1.9:1, at least 2:1, at least 3:1; for example, 1.01:1-1.1:1, 1.01:1-1.25:1, 1.01:1-1.5:1, 1.01:1-1.75:1, 1.01:1-1.8:1, 1.01:1-1.9:1, 1.01:1-2:1, and 1.01:1-3:1; for example, greater than 1:1 and less than 2:1 or 3:1 or 4:1 or 5:1 or 6:1 or the like). The ratio greater than 1:1, such as at least 1.9:1, allows for more consistent sample or droplet expulsion from the opening 106 and reduced sample or droplet wicking along the outer edges/surfaces of the tip 100 proximal to the opening 106.

In one embodiment, the piston 202 and the tip 100 are coaxial with each other, thereby sharing at least one axis 204.

In one embodiment, the sealing fluid 206 is a liquid, such as, for example, a solution, a suspension, an oil, a mineral oil, a liquid metal, a buffer, water, a ferrofluid, silicone, grease, silicone grease, synthetic oil, or the like. In one embodiment, the sealing fluid 206 is a gas. The sealing fluid 206 can be medical grade or food grade.

In one embodiment, the sealing fluid 206 occupies the entire volume of the bore 110. In one embodiment, the sealing fluid 206 occupies the entire volume of the bore 110 less any volume occupied by the piston 202. In one embodiment, the sealing fluid 206 occupies at least a portion of the bore 110 and at least a portion of the opening 106. In one embodiment, the sealing fluid 206 occupies a portion of the bore 110. In one embodiment, the sealing fluid 206 is configured to at least partially fill the bore 110. In one embodiment, the volume and/or location of the sealing fluid 206 changes.

The sealing fluid 206 comprises a first side proximal to the first end 102 of the tip 100 and a second side proximal to the opening 106. The sealing fluid 206 creates a seal between an inner wall of the tip 100 and an outer wall of the piston 202, thereby inhibiting the passage or transfer of material from one side of the sealing fluid 206 to the opposing side of the sealing fluid 206. The sealing fluid 206 inhibits movement or transfer of materials (for example, fluids, analytes, or the like) from one side of the sealing fluid 206 to the other side (for example, such as by forming an internal seal) (or, even out of the first end 102 of the tip 100).

In one embodiment, the sealing fluid 206 can be added, such as by pre-loading the sealing fluid 206 into the tip 100 and then inserting the piston 202 into the tip 100. In one embodiment, the sealing fluid 206 can occupy, such as during pre-loading or priming, the entirety of the bore 110 and the opening 106. In one embodiment, the sealing fluid 206 can be drawn into the tip 100 via the opening 106.

In an embodiment where the sealing fluid 206 is a liquid, the liquid is selected based on the physical properties or characteristics (e.g., viscosity, surface tension, specific density, thermal expansion coefficient, or the like) in relation to at least one of a gap distance ($d_g$) between the outer wall of the piston 202 and the inner wall of the tip 100; the length of a portion of the bore extending from the first side of the sealing fluid 206 to the second end of the tip 100; friction force of the outer wall of the piston 202; friction force of the inner wall of the tip 100; and, combinations thereof; or the like. For example, a viscosity that is too high relative to the gap distance ($d_g$) can create more back pressure than is desired or functional. This could inhibit translation of the piston 202 within the tip 100. Conversely, a viscosity that is too low relative to the gap distance ($d_g$) does not inhibit movement or transfer of materials across the sealing fluid 206 (for example, such as by forming the internal seal) (or, even out of the first end 102 of the tip 100).

The sealing fluid 206 can have a viscosity of 0.2-80,000 mPa-s, including, without limitation, 250-20,000 mPa-s, 1,000-10,000 mPa-s, 2,000-7,500 mPa-s, 2,500-5,000 mPa-s, or 2,550-3,000 mPa-s. In one embodiment, the sealing fluid 206 can have a variable viscosity, for example, when the sealing fluid 206 is a ferrofluid. Therefore, the viscosity can change to accommodate or because of varying forces or pressures, if it desirous to do so.

In one embodiment, the gap distance ($d_g$) has a clearance greater than 0, for example, approximately 0.01 μm to 1 cm (e.g., 0.01-100 μm, 5-50 μm, 0.0125-0.04 mm).

The tip 100 can be any appropriate length ranging from 1 mm to 10 feet. The piston 202 can be any appropriate length ranging from 1 mm to 10 feet. The device or system can have a wide range of sizes because of the manners in which the device or system are capable of being used or implemented. For example, the device or system, such as being sized to fit within a scanning device or onto a lab bench, can be used to pick a sample from a slide. For another example, the device of system, such as being sized to fit within an operating room or doctor's office, can be used (similar to or in conjunction with a catheter) to remove an internal sample (such as a tissue to be biopsied) from a patient or to inject a targeted reagent (e.g., chemotherapy drug; therapeutic drug; or the like) to a patient site.

In one embodiment, the picker head 200 further comprises a mechanical seal (not shown) placed between an outer wall of the piston 202 and an inner wall of the tip 100. The mechanical seal can be, for example, an O-ring, a gasket, or the like.

FIG. 2E shows a first state of the picker head 200 and FIG. 2F shows a second state of the picker head 200. In the example, the picker head 200 has transitioned from the first state to the second state by withdrawing the piston 202 (i.e., moving the piston away from the opening 106). However, the piston 202 can be driven towards the opening 106. In one embodiment, the sealing fluid 206 is displaced.

The location of the sealing fluid 206 can change within the tip 100. For example, as shown in the FIGS. 2E and 2F, the sealing fluid 206 can be displaced towards the first end 102 of the tip 100. However, the sealing fluid 206 can be displaced towards the opening 106 of the tip 100.

In the first state, the picker head 200 includes a first volume $V_1$ which includes the volume of the sealing fluid 206 within $X_1$ ($V_{1,\,sealing\,fluid}$), the volume of the piston 202 within $X_1$ ($V_{1,\,piston}$), and a bore segment 210 which includes any portion of the bore 110 and the opening 106 within $X_1$ not occupied by the sealing fluid 206 or the piston 202 ($V_{1,\,bore\,segment}$).

In the second state, the picker head 200 includes a second volume $V_2$ which is equal to the first volume $V_1$. The first and second volumes $V_1$, $V_2$ (for example, pre-determined volumes) are not tied to any specific feature, structure, or component, but do share the same starting and end points for calculation purposes. In other words, the first and second volumes $V_1$, $V_2$ are functions of the distances within the cross-sections depicted by $X_1$ and $X_2$ (for example, pre-determined distances). As depicted in FIG. 2E, the first volume $V_1$ extends from the external side of the opening 106 to a given distance inside the bore 110 (for example, in FIG. 2E, the distance extends into a portion of the sealing fluid 206). As depicted in FIG. 2F, the second volume $V_2$ extends from the external side of the opening 106 to the same given distance into bore 110 (for example, in FIG. 2F, the sealing fluid 206 has been displaced towards the first end 102 of the tip 100 and is no longer present at that location).

Though the first and second volumes are equal ($V_1=V_2$), the component volumes forming the second volume $V_2$ can be different than the component volumes of the first volume $V_1$. The second volume $V_2$ includes the volume of the sealing fluid 206 within $X_2$ ($V_{2,\,sealing\,fluid}$), the volume of the piston 202 within $X_2$ ($V_{2,\,piston}$), and a bore segment 210 which includes any portion of the bore 110 and the opening 106 within $X_2$ not occupied by the sealing fluid 206 or the piston 202 ($V_{2,\,bore\,segment}$). As shown in FIGS. 2E and 2F, due to the transition, the $V_{sealing\,fluid}$ is less in the second state than in the first state; $V_{piston}$ is less in the second state than in the first state; and $V_{bore\,segment}$ is greater in the second state than in the first state.

The sealing fluid 206 can be selected to satisfy the condition given by:

$$V_1 = V_2; \quad (1)$$

$$V_{1,sealing\ fluid} + V_{1,piston} + V_{1,bore\ segment} = V_{2,sealing\ fluid} + V_{2,piston} + V_{2,bore\ segment}; \quad (2)$$

The change in volume of the sealing fluid 206 can be a function of (1) the physical properties or characteristics of the sealing fluid 206; (2) the gap distance ($d_g$); (3) the length of a portion of the bore extending from the first side of the sealing fluid to the second end of the tip; (4) friction force of the outer wall of the piston 202; (5) friction force of the inner wall of the tip 100; and (6) combinations of (1)-(5).

In other words, the sealing fluid 206 can be selected to satisfy the condition given by:

$$\Delta V_{sealing\ fluid} + \Delta V_{piston} + \Delta V_{bore\ segment} = 0$$

wherein $\Delta V_{sealing\ fluid}$ represents a change in volume of the sealing fluid within a pre-determined portion of the picker head when the piston is moved from a first state to a second state; wherein $\Delta V_{piston}$ represents a change in volume of the piston within the pre-determined portion of the picker head when the piston is moved from the first state to the second state; and wherein $\Delta V_{bore\ segment}$ represents a change in volume of a bore segment comprising any portion of the bore and the opening within the pre-determined portion of the picker head not occupied by the sealing fluid or the piston when the piston is moved from the first state to the second state.

The change in volume of the sealing fluid 206 can be a function of (1) the physical properties or characteristics of the sealing fluid 206; (2) the gap distance ($d_g$); (3) the length of a portion of the bore extending from the first side of the sealing fluid to the second end of the tip; (4) friction force of the outer wall of the piston 202; (5) friction force of the inner wall of the tip 100; and (6) combinations of (1)-(5).

Figure 2G:
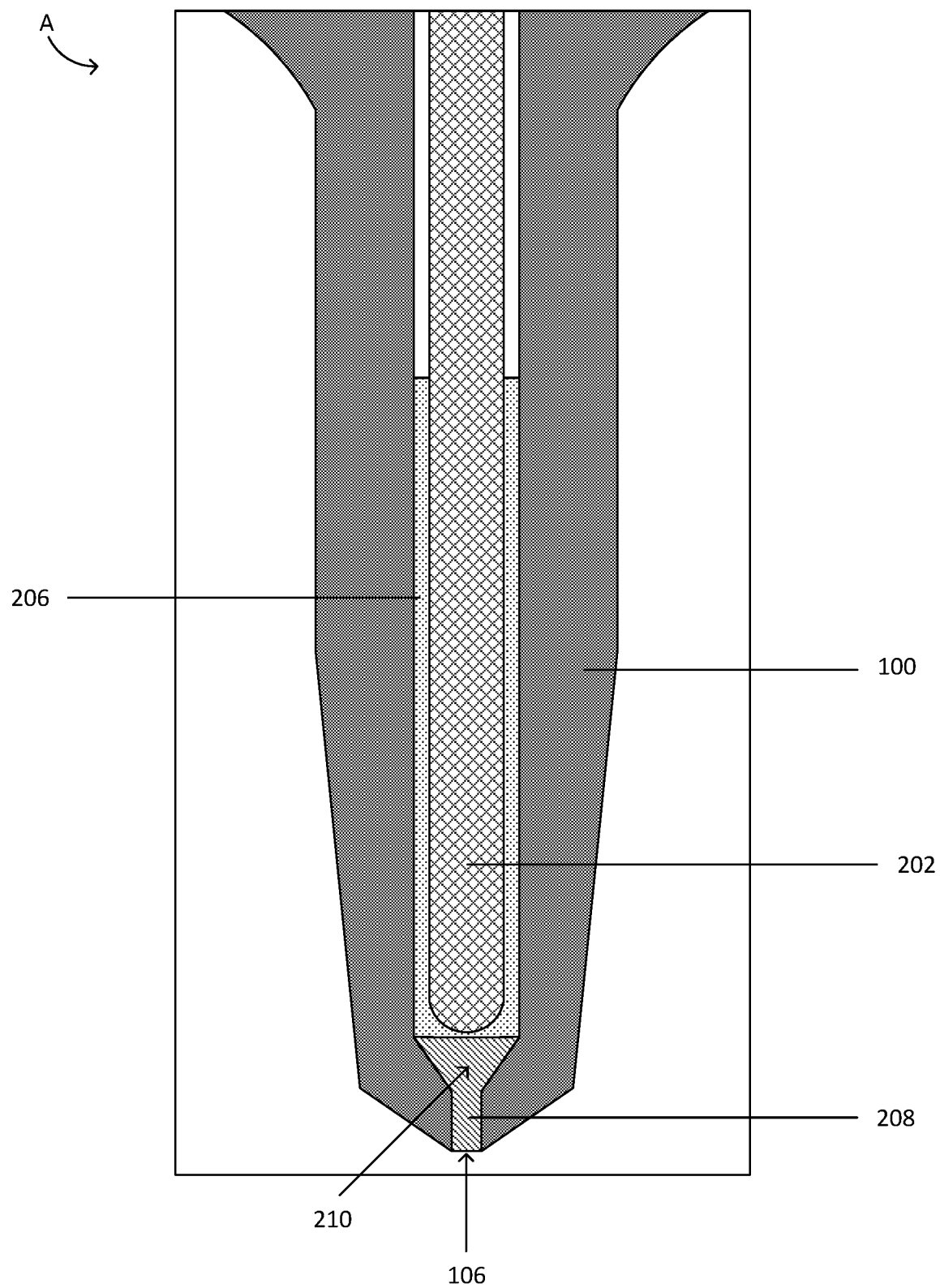
FIG. 2G shows an example picker head.

Alternatively, to allow for piston 202 translation within the tip 100 and to inhibit movement of materials or analytes across the sealing fluid 206, the force exerted by or on certain elements satisfy the condition given by:

$$F_{DSF} > F_{DBS}$$

where $F_{DSF}$ represents the force to displace the sealing fluid 206 within the tip 100; and where $F_{DBS}$ represents the force to displace the fluid or material within the bore segment 210. In other words, the force required to displace the sealing fluid 206 is greater than the force required to displace the fluid or material within the bore segment 210. In one embodiment, the fluid is a gas (for example, air, nitrogen, or the like). In one embodiment, and as shown in FIG. 2G, the fluid is a liquid. As further discussed herein, the force required to displace the sealing fluid 206 can be a function of (1) the physical properties or characteristics of the sealing fluid 206 such as viscosity or surface tension; (2) the gap distance ($d_g$); (3) the length of a portion of the bore extending from the first side of the sealing fluid 206 to the second end of the tip 100; (4) friction force of the outer wall of the piston 202; (5) friction force of the inner wall of the tip 100; and (6) combinations of (1)-(5). For example, the requisite force can be increased with a smaller gap distance and/or with the sealing fluid 206 having a higher viscosity, whereas the requisite force can be decreased with a larger gap distance and/or with the sealing fluid 206 having a lower viscosity. As another example, coatings on the outer wall of the piston 202 and/or the inner wall of the tip 100 can increase or decrease the requisite force, such as by reducing frictional forces thereby reducing shear stresses on the sealing fluid 206.

Furthermore, the sealing fluid 206 can be selected to be biocompatible (i.e., to allow for interactions with biological materials without degrading or altering the properties or characteristics of the biological materials) and/or sterilizable (i.e., to allow for sterilization without degrading or altering the properties or characteristics of the sealing fluid 206).

In one example, the sealing fluid is mineral oil having a viscosity of 2500-2600 mPa-s and the gap distance is 0.0125-0.04 mm. In another example, the sealing fluid is mineral oil having a viscosity of 7600-7700 mPa-s and the gap distance is 0.0375-0.12 mm. In yet another example, the sealing fluid is silicone grease having a viscosity of 900-1000 mPa-s and the gap distance is 0.0045-0.016 mm.

As shown in FIG. 2G, one of the opening 106 and/or the bore segment 210 can be at least partially filled (i.e., filled at least 0.1%, 1%, 2%, 3%, 4%, 5%, 10%, 15%, 20%, 25%, 30%, 33%, 40%, 50%, 60%, 70%, 75%, 80%, 90%, 99%, or 100%) with a hydraulic fluid 208 to fluidically couple the piston 202 and the tip 100. The hydraulic fluid 208 can be incompressible or have low compressibility. In one embodiment, the hydraulic fluid 208 can be a liquid, such as, for example, a solution, a suspension, an oil, a mineral oil, a liquid metal, a buffer, water, a ferrofluid, grease, silicone grease, synthetic oil, or the like. In one embodiment, the hydraulic fluid 208 is a gas. The hydraulic fluid 208 can be medical grade or food grade.

Furthermore, the hydraulic fluid 208 can be selected to be biocompatible (to allow for interactions with biological materials without degrading or altering the properties or characteristics of the biological materials) and/or sterilizable (to allow for sterilization without degrading or altering the properties or characteristics of the hydraulic fluid 208).

In one embodiment, the hydraulic fluid 208 and the sealing fluid 206 can be the same liquid. In one embodiment, the hydraulic fluid 208 and the sealing fluid 206 are different liquids. The hydraulic fluid 208 and the sealing fluid 206 can be inert and/or immiscible with each other.

In one embodiment, at least one section of the piston 202 includes at least one coating that repels or attracts a liquid, such as the hydraulic fluid 208 and/or the sealing fluid 206. In one embodiment, at least one section of the bore 110 includes at least one coating that repels or attracts a liquid, such as the hydraulic fluid 208 and/or the sealing fluid 206. In one embodiment, at least one section of the bore 110, such as bore segment 210, includes at least one coating that repels or attracts a liquid, such as the hydraulic fluid 208 and/or the sealing fluid 206. In one embodiment, at least one section of the opening 106 includes at least one coating that repels or attracts a liquid, such as the hydraulic fluid 208 and/or the sealing fluid 206. In one embodiment, at least one section of the piston 202 can include a coating which repels a liquid, such as the hydraulic fluid 208 and/or the sealing fluid 206, and at least one section of the bore 110 includes a coating which attracts the liquid, such as the hydraulic fluid 208 and/or the sealing fluid 206. For example, it may be desirous to have a coating on the piston 202 which repels a sealing liquid, whereas a coating on the bore 110 and/or the opening 106 attracts the hydraulic fluid 208. In one embodiment, coatings of the respective components can be selected to repel or attract the same liquid or different liquids. For example, it may be desirous to have a coating on the piston 202 to repel the sealing fluid 206, a coating on the bore 110 and a coating on the opening 106 that attracts the target material.

The piston 202 can be composed of a variety of different materials comprising, but not limited to, ceramics; glass; metals; organic or inorganic materials; plastic materials; and combinations thereof.

Gripper/Support

Figure 3A:
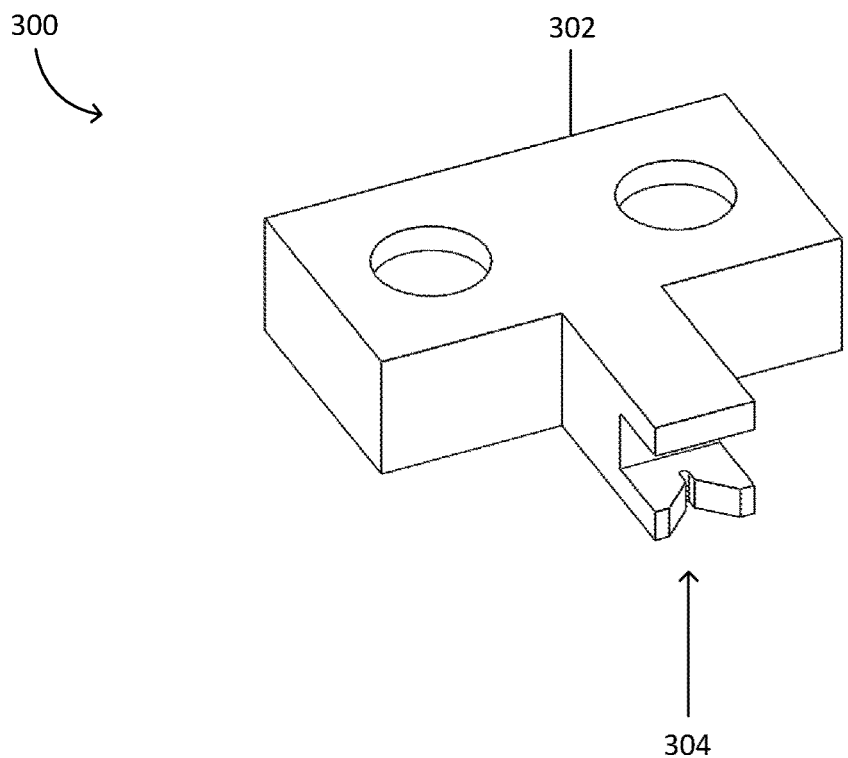
FIGS. 3A-3D show example grippers.

FIG. 3A show a gripper 300 configured to couple the picker head 200 to a driver or another component. The gripper 300 comprises a base 302 and a clasp 304 to engage at least one segment of the picker head 200, such as the piston 202. The clasp 304 extends outwardly from the base 302. The clasp 304 engages with a portion of the piston 202. The clasp 304 can be a top plate and a bottom plate with a notch sized and shaped to accept the main body of the piston 202 with a space between the top and bottom plates (for example, to accept an enlarged end of the piston 202). The base 302 is sized and shaped to be attached directly or indirectly to a driver (not shown).

Figure 3B:
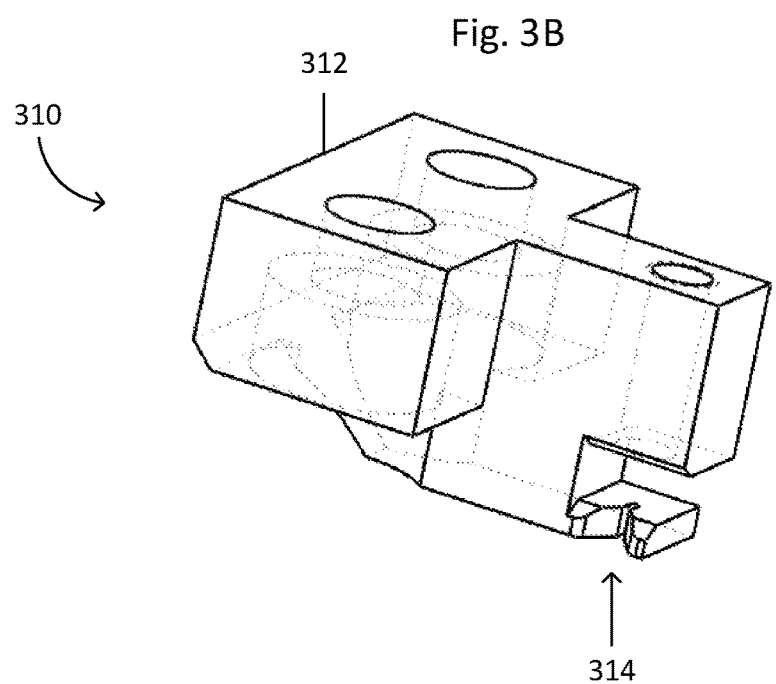

FIG. 3B shows a gripper 310. The gripper 310 comprises a base 312 and a clasp 314. The gripper 310 is substantially identical to the gripper 300, except that the clasp 314 is oriented in direction different than the clasp 304 relative to the base 312.

Figure 3C:
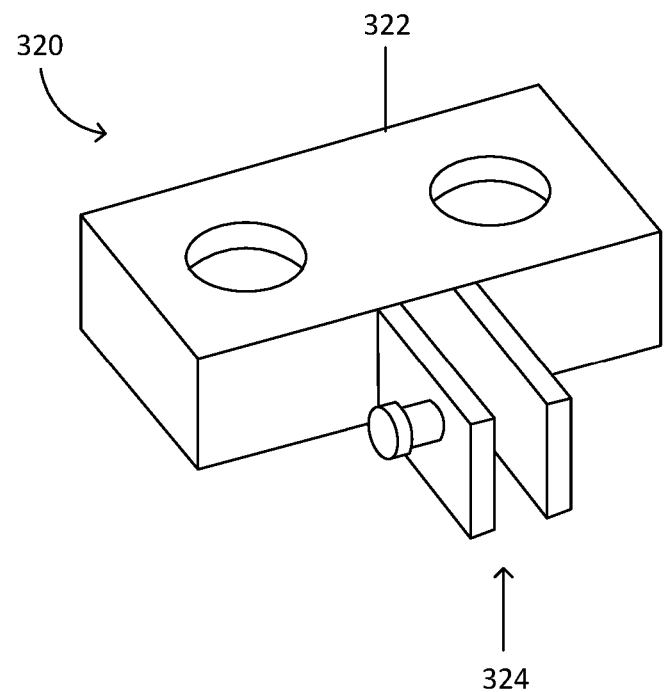

FIG. 3C shows a gripper 320. The gripper 320 comprises a base 322 and a clasp 324. The clasp 324 is a bracket comprising a set screw, such that the set screw is configured to engage and secure the picker head 200 or a segment thereof, comprising, without limitation, the piston 202.

Figure 3D:
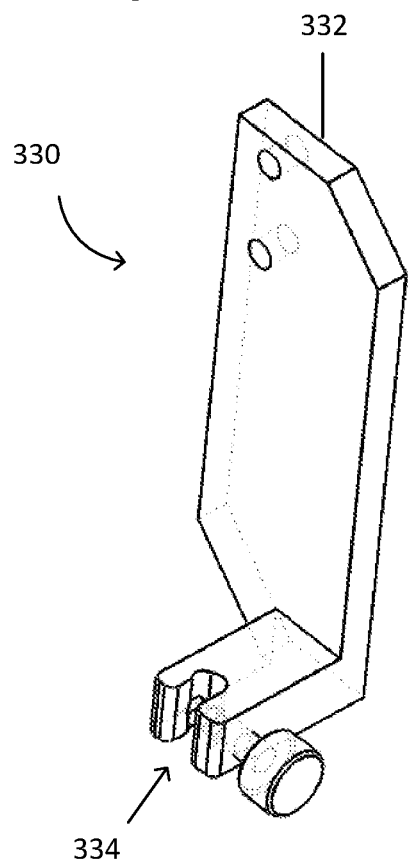

FIG. 3D shows a gripper 330. The gripper 330 comprises a base 332 and a clasp 334. The gripper 330 is substantially identical to the gripper 320, except that the clasp 334 is oriented in direction different than the clasp 324 relative to the base. In one embodiment, the base 332 is more elongated.

In one embodiment, the gripper 300 couples the picker head 200 to a driver (not shown), such as a servomotor, a stepper motor, a piezo-electric actuator, a solenoid, or the like. In one embodiment, a plurality of grippers is used to couple the picker head 200 to a plurality of components. In one embodiment, a plurality of grippers is used to couple different segments of the picker head 200 to the same component. For example, a first gripper couples the picker head 200 to a motor (for example, couples the piston 202 to drive the piston 202); and a second gripper couples the picker head 200 to a stationary component (for example, couples the second end 104 or the tip 100 to a bracket or the like to stabilize the picker head, so as to inhibit undesired movements, vibrations, oscillations, or the like).

Figure 4A:
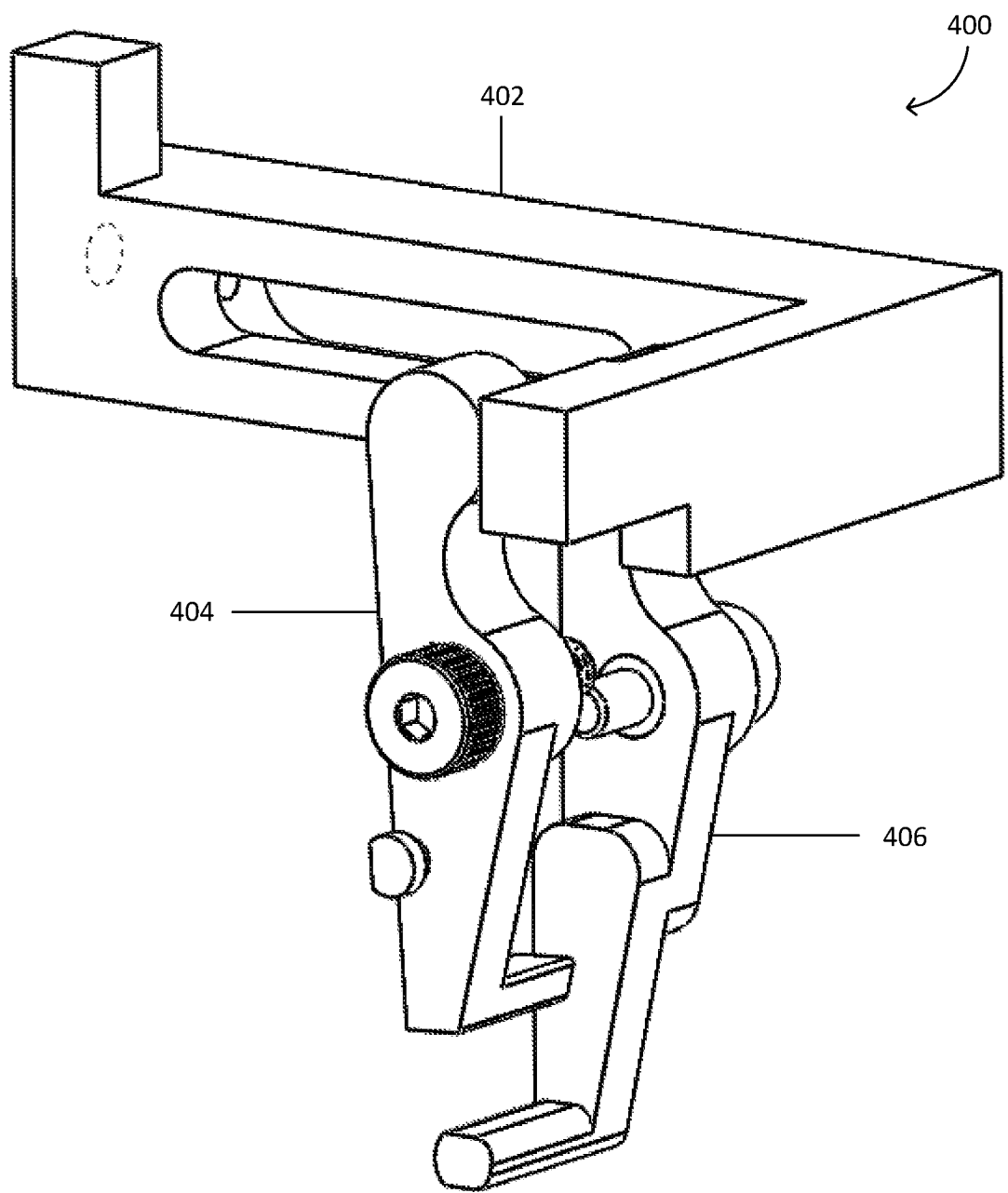
FIGS. 4A-4B show an example gripper.
Figure 4B:
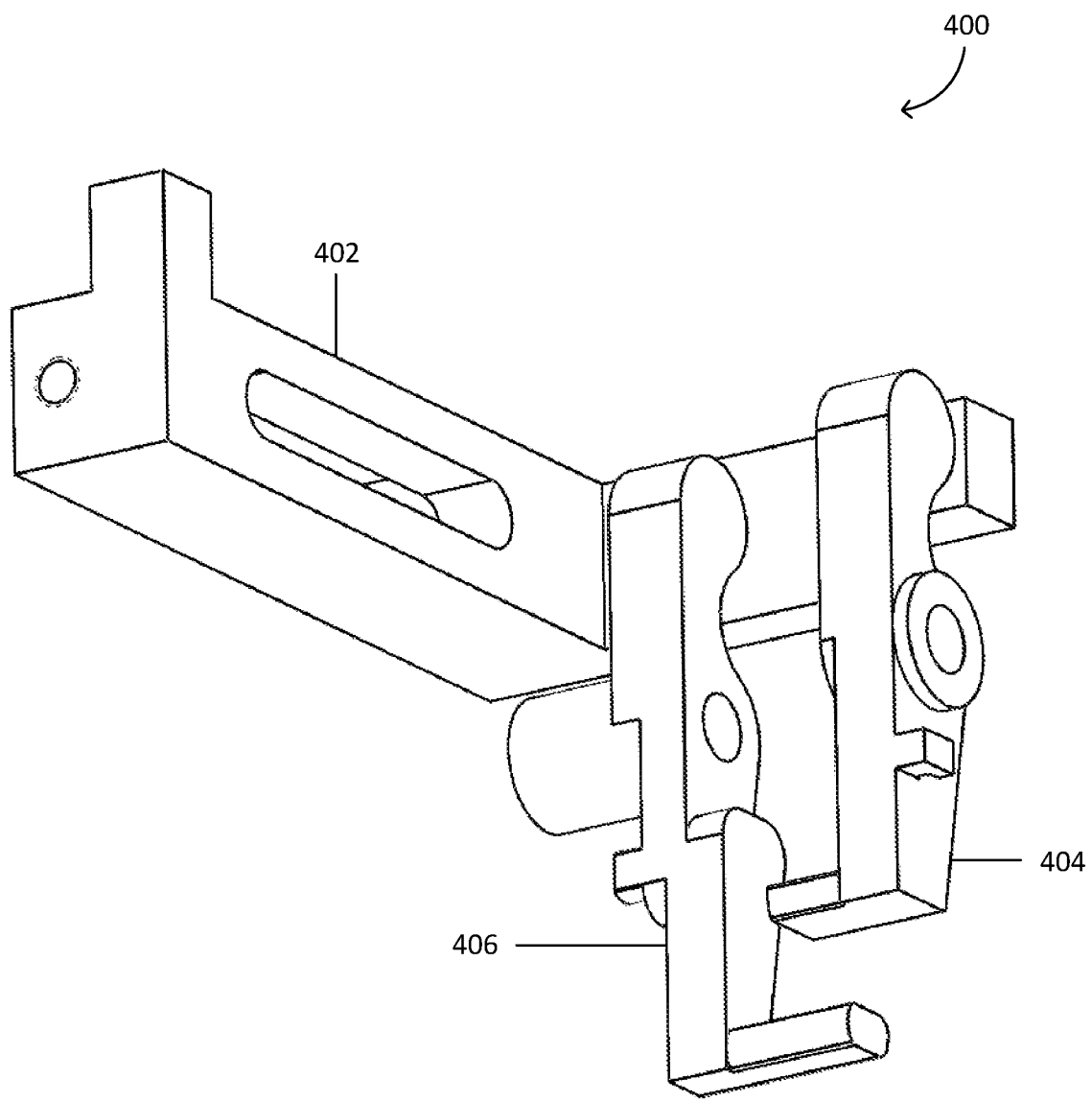

FIGS. 4A-4B show a gripper 400. The gripper 400 comprises a base 402, a first lever 404 comprising at least one finger, and a second lever 406 comprising at least one finger. When the base 402 is moved towards the first and second levers 404, 406, the base 402 pushes on a portion of each of the first and second levers 404, 406, thereby causing each to rotate about an axis. In doing so, the fingers of the first and second levers 404, 406 are moved into an "open" position. Conversely, when the base 402 is moved away from the first and second levers 404, 406, springs (not shown; see FIGS. 8A-8C) pull on each of the first and second levers 404, 406 to return the fingers to a "closed" position. When in the "closed" position, the finger of the first lever 404 engages the first end of the piston 202 thereby securing the first end of the piston 202 against a headblock (not shown; see FIGS. 8A-8C). The tip 100 is secured by the finger of the second lever 406 against a catch of a support (not shown; see FIGS. 5, 8A-8C). The "open" position allows for insertion and removal of the picker head 200. The "closed" position allows the picker head 200 to be secured and engaged for movement of the piston 202. For example, the base 402 can be driven along an axis perpendicular to the first and second levers 404, 406 by an actuator (not shown; see FIGS. 8A-8C) to move from the "closed" position to the "open" position or to cause to move from the "open" position to the "closed" position.

In one embodiment, the first and second levers 404, 406 are independently connected to the base 402. In one embodiment, the first and second levers 404, 406 are jointly connected to the base 402.

Figure 5:
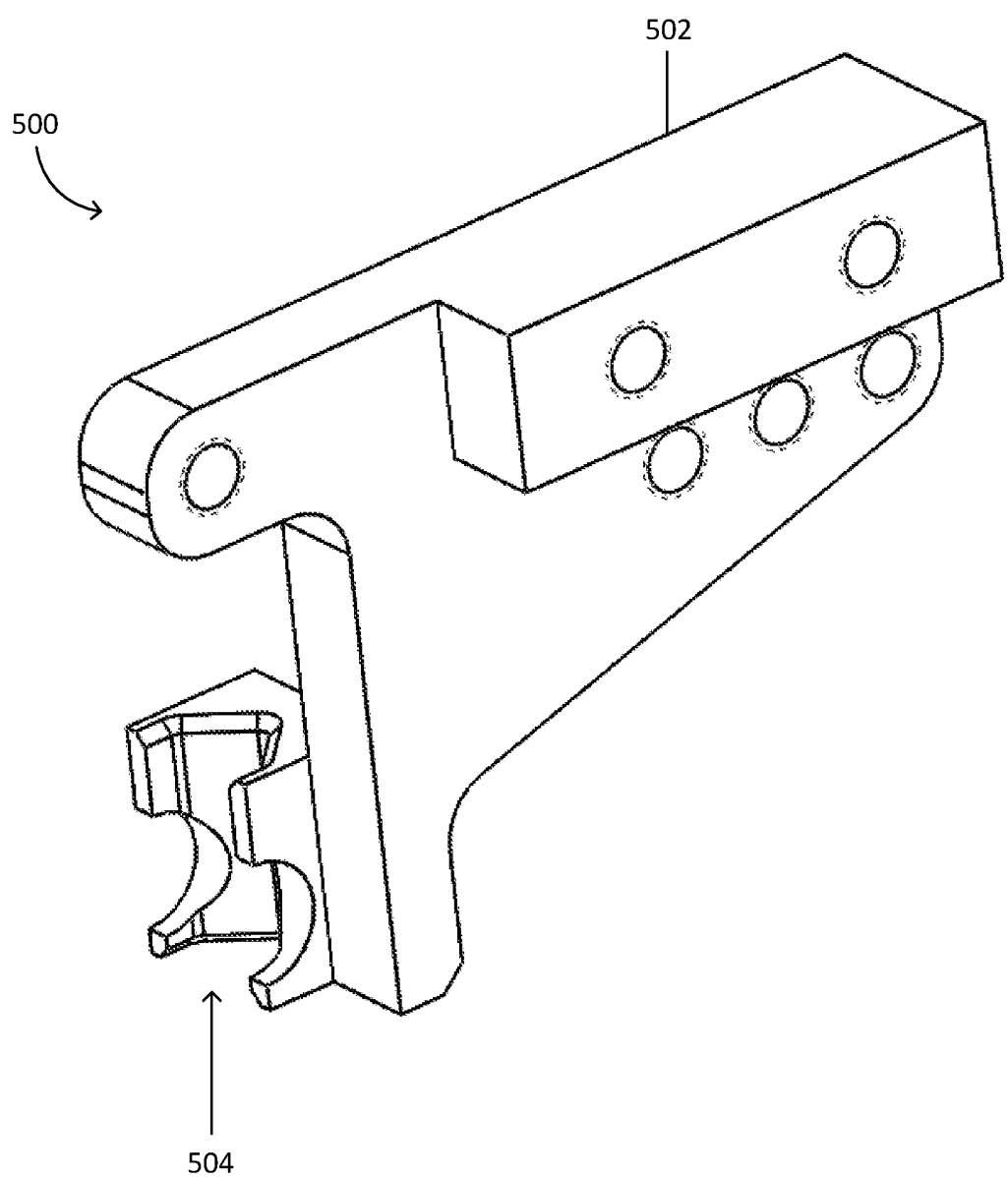
FIG. 5 shows an example support.

FIG. 5 shows a support 500. The support 500 comprises a base 502 and a catch 504. The catch 504 is shaped and configured to hold the tip 100. For example, the catch 504 can include one or more mechanical arms, a claw, fingers, combinations thereof, and the like. The base 502 attaches the catch 504 to a portion of a picking system.

The gripper 300, 310, 320, 330 and the support 400 can be composed of a variety of different materials including, but not limited to, ceramics; glass; metals; organic or inorganic materials; plastic materials; polymers; jewels (i.e. ruby, sapphire, or diamond); combinations thereof; and the like.

Picker

Figure 6:
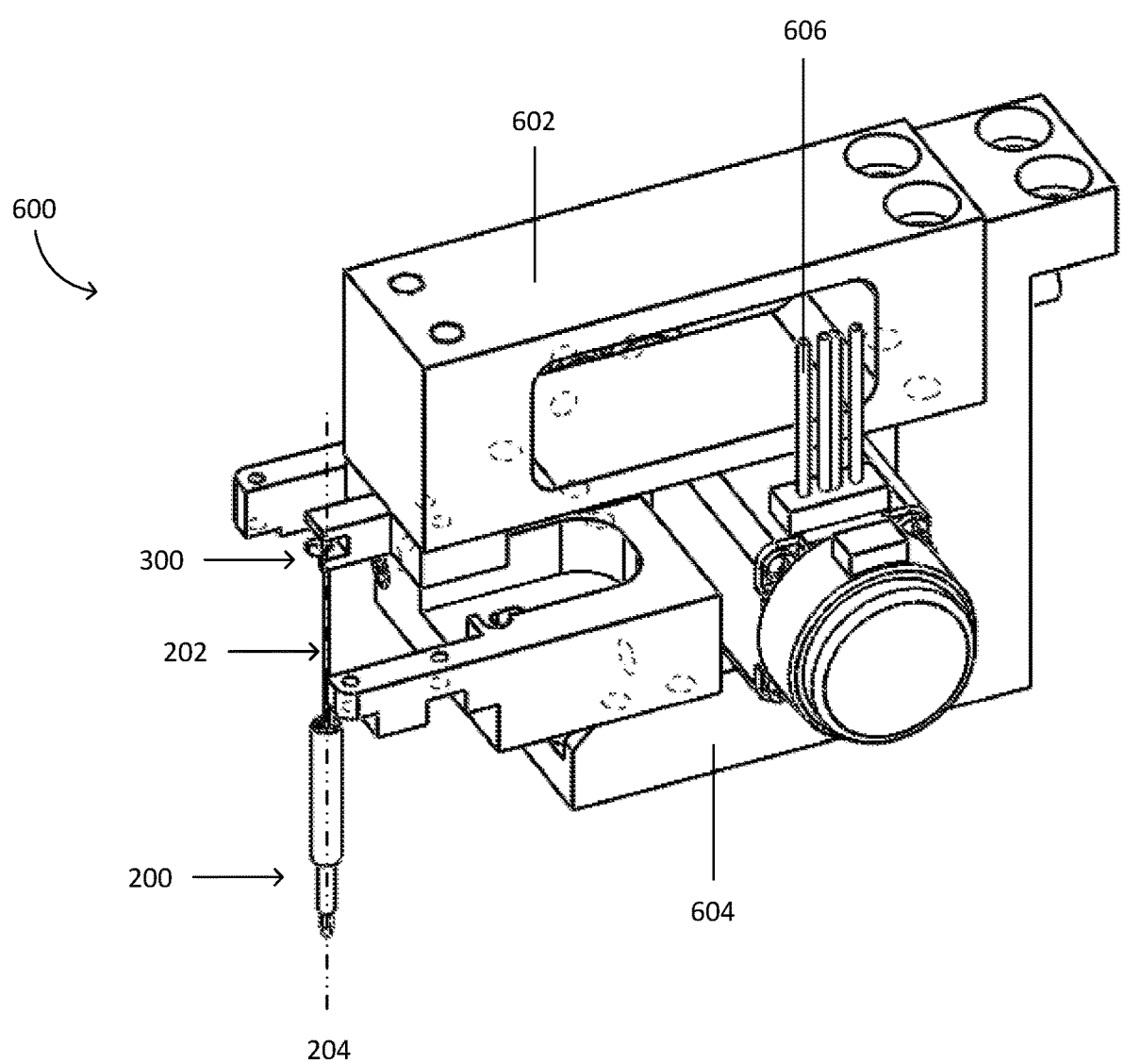
FIG. 6 shows an example picking system.

FIG. 6 shows a picker 600. The picker 600 comprises the picker head 200, the gripper 300, and a driver 602. The driver 602, via the gripper 300, moves the piston 202 along the axis 204 or causes the piston 202 to move along the axis. The driver 602 can be a motor, such as a servomotor, a stepper motor, a piezo-electric actuator, a solenoid, or the like. The driver 602 provides high resolution control of the piston 202. The driver 602 can also provide a rapid response (for example, to allow for oscillation) and can be operated in an open or closed loop. The driver 602 can provide motion along the x, y, and z axes or may provide motion along only one axis. The driver 602 can move the piston 202 from 1 nanometer to 100 millimeters along axis 204, comprising, without limitation, up to 10 nm, 100 nm, 1 µm, 10 µm, 25 µm, 50 µm, 100 µm, 200 µm, 250 µm, 500 µm 750 µm, 1 mm, 10 mm, 25 mm, 50 mm, or 100 mm. The movement of the piston 202 along the axis 204 by driver 602 can draw in or expel a volume of up to 1 picoliter, 10 picoliters, 100 picoliters, 1 nanoliter, 10 nanoliter, 100 nanoliters, 1 microliter, 10 microliters, 100 microliters, or 1 milliliter.

The picker 600 can also comprise a mount 604 to attach the picker head 200, the gripper 300, and the driver 602 to an imaging or detection system, such as a scanner or a microscope. The mount 604 can be stationary within the imaging or detection system or may be attached to the second actuator (not shown) within the imaging or detection system, such as to move the picker 600 along any appropriate axis.

The picker 600 can also comprise a driver knob (not shown) for manual operation and/or wire leads 606 for automated operation. Manual operation can comprise adjustments or movements of the driver 602 or the second actuator (not shown) by hand or may comprise motorized adjustments or movements to the picker or picking by an operator via a manual controller, such as a touch screen, a joystick, a directional pad or the like. Automated operation can comprise adjustments or movements of the driver 602 or the second actuator (not shown) by a controller or processor based on instructions, processes, or algorithms of a non-transitory computer program.

Additionally, the picker head 200 can be replaced by manual operation (i.e., changing out by hand) or by automated operation (i.e., by expelling the used picker head, mating or inserting a new picker head, raising the picker, and returning to a desired position).

The gripper 300 can be attached to the driver 602 by bolts, screws, dowels, adhesive, epoxy, tongue-and-groove joint, dovetail joint, or any appropriate means or method by which to attach or join two pieces.

In one embodiment, the pressure exerted by the driver 602 can be a function of speed at which the driver 602 causes the piston 202 to translate along the axis 204.

Figure 7:
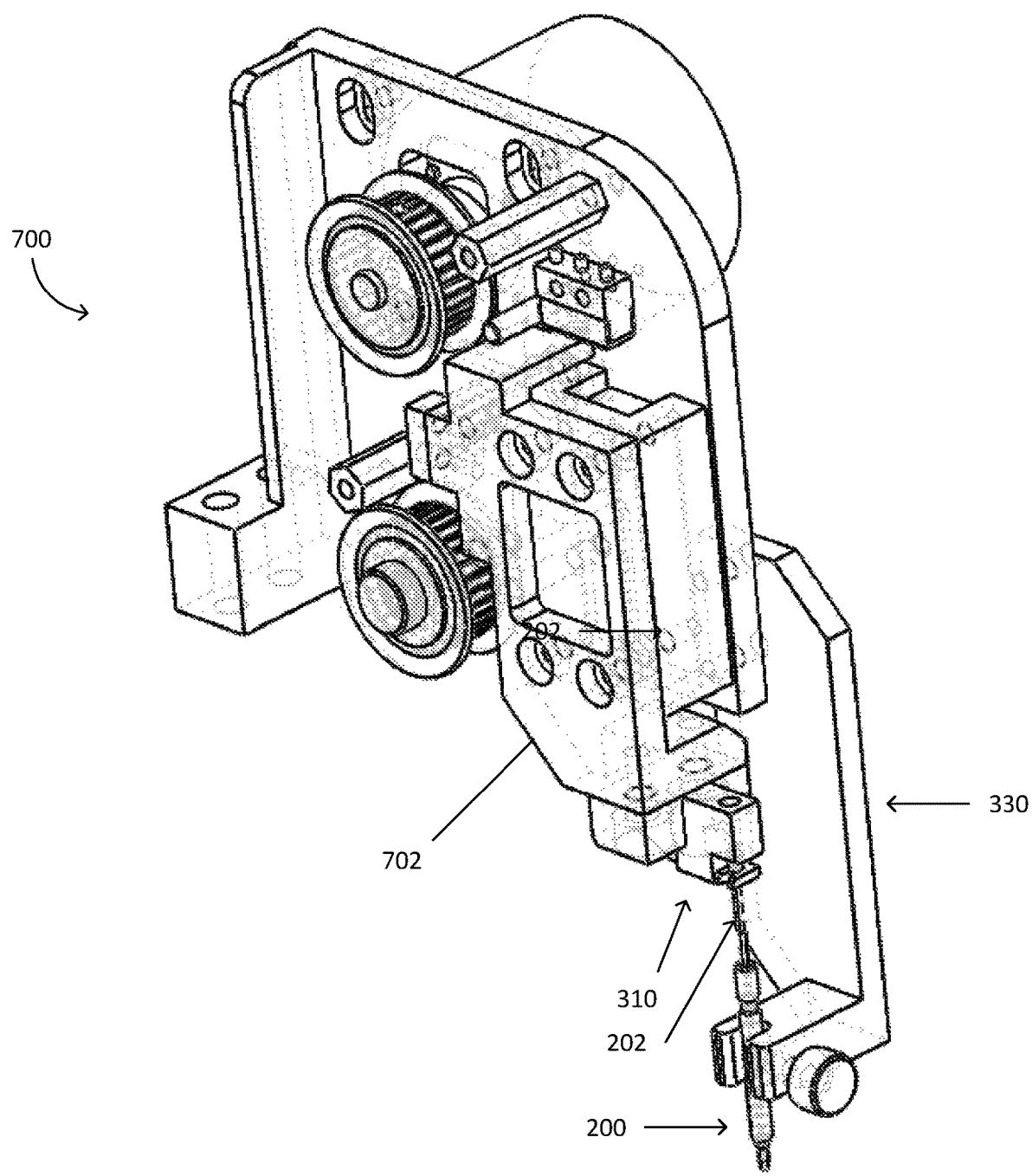
FIG. 7 shows an example picking system.

FIG. 7 shows a picker 700. The picker 7 is substantially identical to the picker 600, except that the picker head 200 is engaged and secured by a gripper 310 and a gripper 330. Additionally, a driver 702 is shown.

Figure 8A:
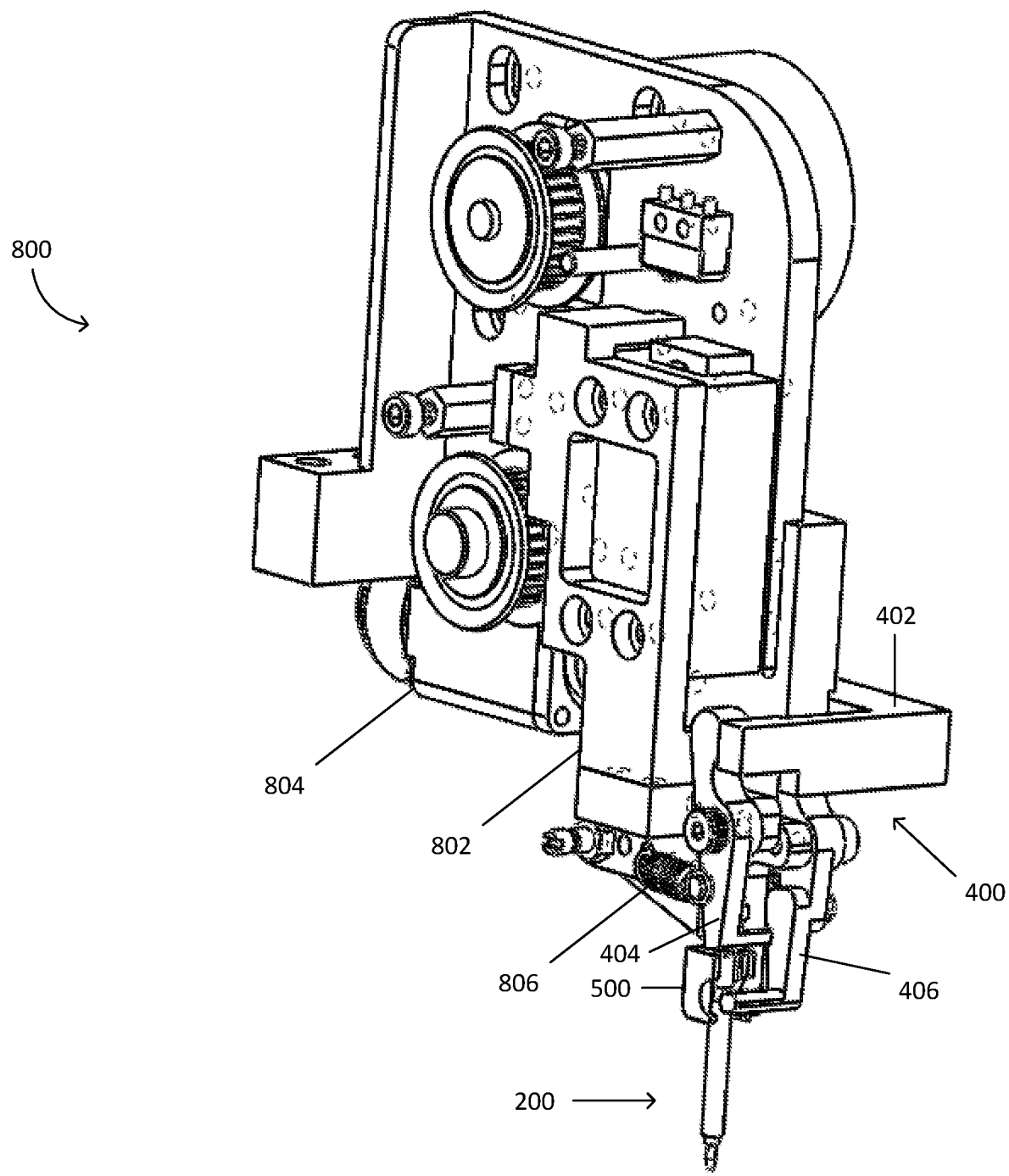
FIGS. 8A-8C show an example picking system.
Figure 8B:
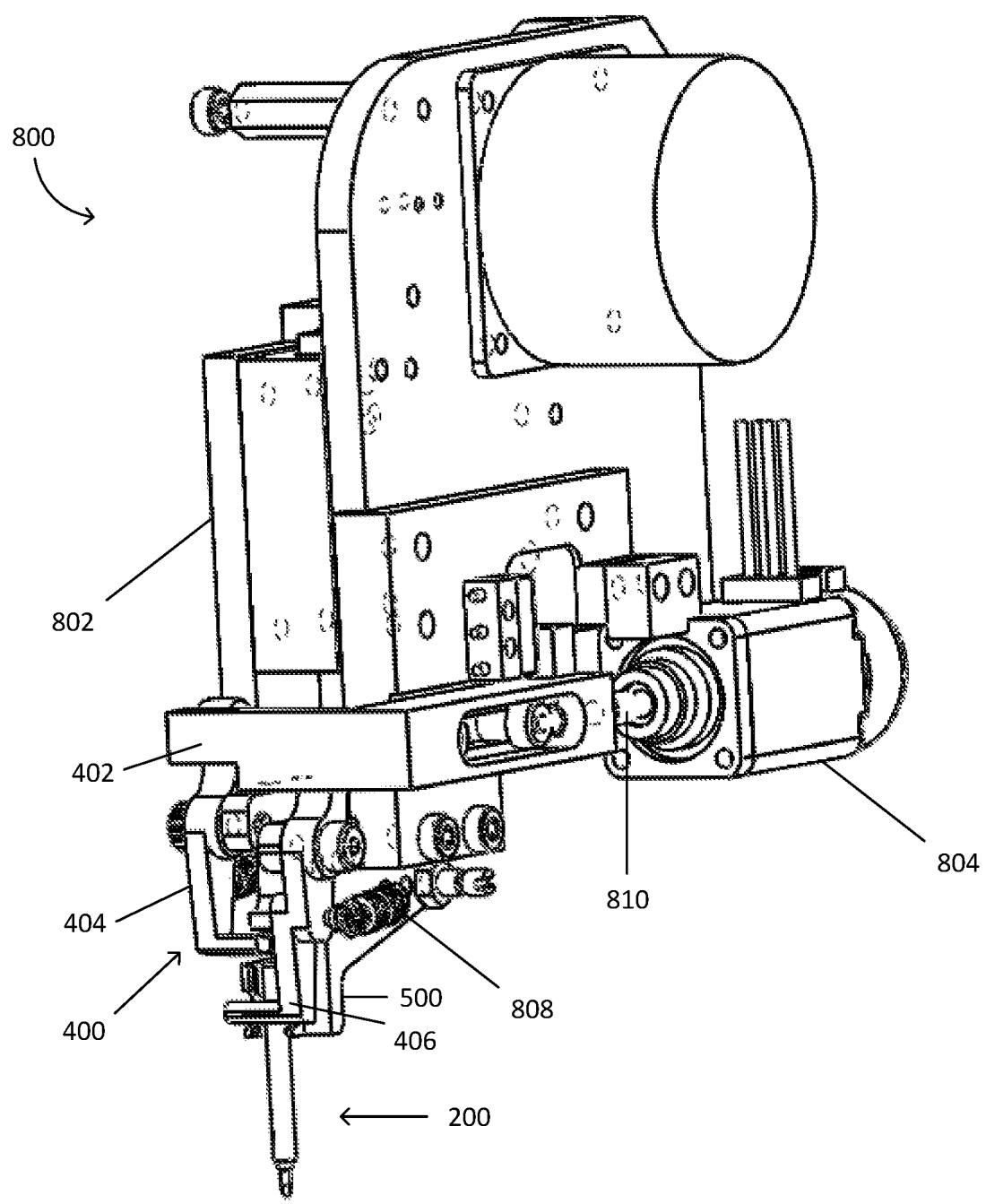
Figure 8C:
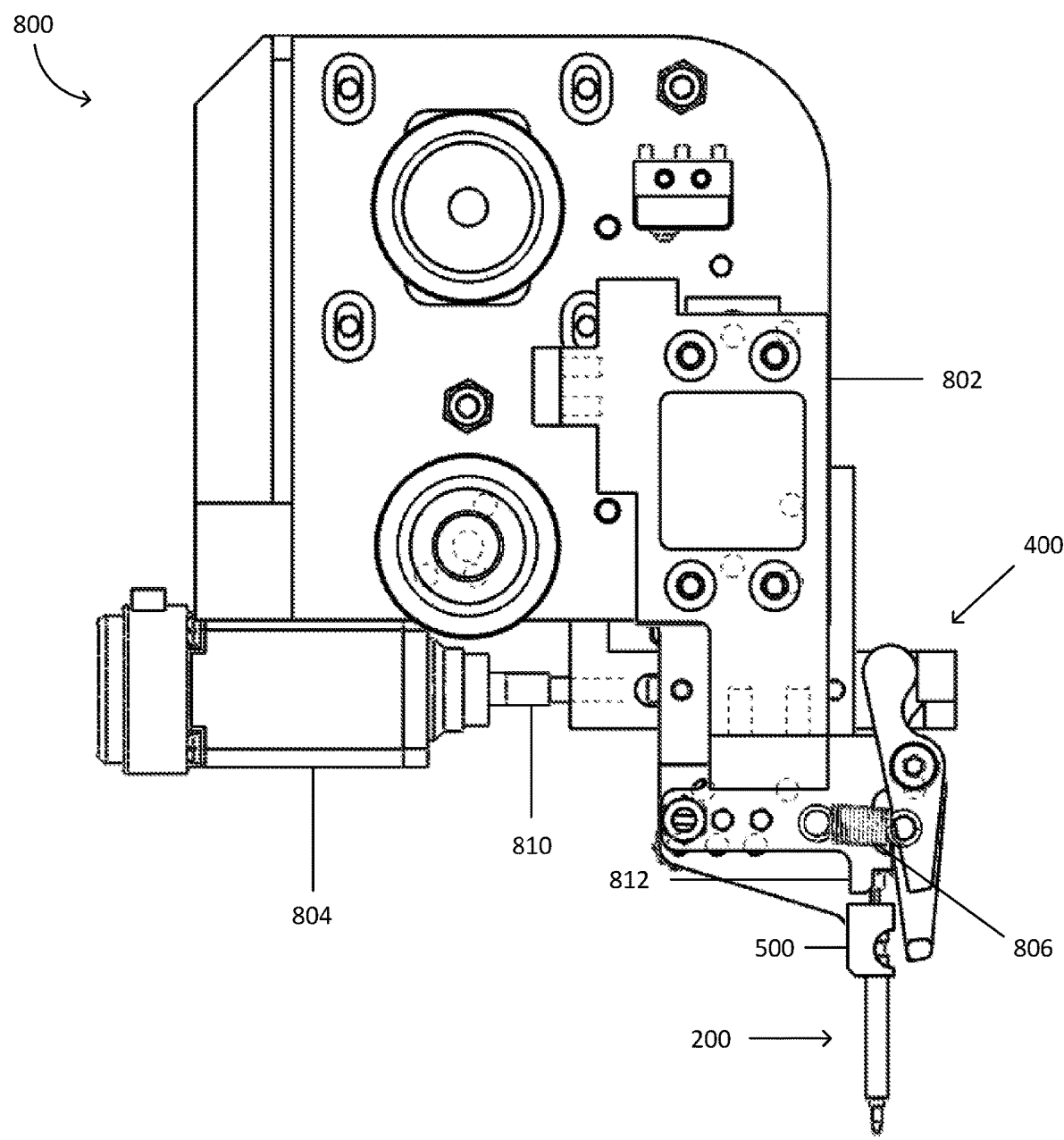

FIGS. 8A-8C show a picker 800. The picker 800 is substantially identical to the picker 700, except that the picker head 200 is engaged and secured by the gripper 400. When the base 402 is moved towards the first and second levers 404, 406, the base 402 pushes on a portion of each of the first and second levers 404, 406, thereby causing each to rotate about an axis. In doing so, the fingers of the first and second levers 404, 406 are moved into an "open" position. Conversely, when the base 402 is moved away from the first and second levers 404, 406, springs 806, 808 pull on each of the first and second levers 404, 406 to return the fingers to a "closed" position. When in the "closed" position, the finger of the first lever 404 engages the first end of the piston 202 thereby securing the first end of the piston 202 against a headblock 812. The tip 100 is secured by the finger of the second lever 406 against a catch of a support 500. The "open" position allows for insertion and removal of the picker head 200. The "closed" position allows the picker head 200 to be secured and engaged for movement of the piston 202. For example, the base 402 can be driven along an axis perpendicular to the first and second levers 404, 406 by a motor 804 and/or an actuator 810 to move from the "closed" position to the "open" position or to cause to move from the "open" position to the "closed" position. When in the "closed" position, the finger of the first lever 404 engages the first end of the piston 202 thereby securing the first end of the piston 202 against a headblock 812. The tip 100 is secured by the finger of the second lever 406 against the catch 504 of a support 500. The "closed" position allows the picker head 200 to be secured and engaged for movement of the piston 202. The picker 800 further comprises a driver 802 to translate the piston 202 along the axis 204. The driver 802 is connected to the headblock 812 and the first lever 404. For example, in the "closed" position, the driver 402 drives the headblock 812 and the first lever 404, which, in turn, causes the piston 202 to translate along the axis 204.

The picker 800 further allows for homing of the piston 202 within the tip 100 (for example, thereby permitting the location of the second end of the piston 202 to be known relative to the portion of the inner wall 112 of the tip 100 proximal to the opening 106). For example, to home the piston 202, the picker head 200 is inserted (whether manually by an operator/user or automatically by a loading mechanism) into the gripper 400. The gripper 400 is retained in the "open" position. The first end of the piston 202 is engaged by the headblock 812. The headblock 812 is driven toward the tip 100, thereby causing the piston 202 to be driven toward the opening 106. When the piston 202 contacts the portion of the inner wall 112 of the tip 100 proximal to the opening 106, the piston 202 is not able to translate any further toward the opening 106. The headblock 812 stops being driven (for example, via feedback) and the gripper 400 is moved to the "closed" position, whereby the finger of the first lever 404 engages the piston 202 and the finger of the second lever 406 engages the tip 100. Alternatively, the finger of the second lever 406 engages the tip 100 while the piston 202 is being driven within the tip 100 via the headblock 812 for homing purposes.

After homing the piston 202, the piston 202 can be retracted. The position of the piston 202, such as when homed, can be recorded, such as by an encoder.

Method(s) for Using a Picker

The picker 800 can be used to isolate or collect a target material from a sample. A picking system comprising the picker 800 and a stage or substrate holder (not shown) can be used. The picker 800 can be attached to one or more actuators 810 to move the picker 800 along one or more axes. The stage or substrate holder (not shown) can be attached to an actuator (not shown) to move the stage or substrate holder (not shown) along at least one axis. Alternatively, the stage or substrate holder (not shown) can be attached to multiple actuators, each actuator configured to move the stage or substrate holder (not shown) along at least one axis. The stage or substrate holder (not shown) can be attached, directly or indirectly, to the mount 604; or, the stage or substrate holder (not shown) can be attached to a second mount (not shown) to attach the stage or substrate holder (not shown) to the same imaging or detection device as the picker 800.

The sample can be placed on a substrate, such as a well plate, a slide, or the like, or into a vessel, such as a tube. The substrate or vessel can be imaged to detect the target material and determine the location of the target material. After determining the location of the target material, the picker head 200 is brought proximal to the target material. A force, such as a negative pressure gradient, can be introduced by the picker head 200, such as by moving the piston 202 away from the opening 106 of the tip 100, thereby causing the target material to be drawn into or through the opening 106 of the tip 100. An opposite force, such as a positive pressure gradient, can be introduced by the picker 100, such as by moving the piston 202 toward the opening 106 of the tip 100, thereby causing the target material or a wetting fluid (e.g., the hydraulic fluid or a different fluid) to be expelled from or through the opening 106 of the tip 100. In one embodiment, when the wetting fluid is used, the wetting fluid may be added to the sample proximal to or directly on the target material prior to introducing the negative pressure gradient.

After withdrawing the target material from the substrate or vessel, the target material can be moved to and expelled onto or into a secondary substrate or vessel. The target material can then be analyzed using any appropriate analysis method or technique.

It should be understood that the target material can be any appropriate biological sample or fraction thereof. In one embodiment, the sample or fraction thereof can be blood (including buffy coat), bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. In one embodiment, the sample or fraction thereof can be tissue or a material from adipose tissue, an adrenal gland, bone marrow, a breast, a caudate, a cerebellum, a cerebral cortex, a cervix, a uterus, a colon, an endometrium, an esophagus, a fallopian tube, a heart muscle, a hippocampus, a hypothalamus, a kidney, a liver, a lung, a lymph node, an ovary, a pancreas, a pituitary gland, a prostate, a salivary gland, a skeletal muscle, skin, a small intestine, a large intestine, a spleen, a stomach, a testicle, a thyroid gland, a bladder, or any appropriate tissue source, including tumor tissue. The tissue sample can have a thickness of 0.5 µm to 50 µm. The tissue sample can be frozen, formalin-fixed paraffin-embedded, hydrated, dry, or any other appropriate manner in which to prepare the tissue sample.

It should also be understood that the target material can be a cell, such as ova or a circulating tumor cell ("CTC"), a nucleated red blood cell, a fetal cell, a circulating endothelial cell, a vesicle, a liposome, a protein, a nucleic acid, a biological molecule, a naturally occurring or artificially prepared microscopic unit having an enclosed membrane, a parasite, a microorganism, or an inflammatory cell.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/". As used herein, the term "one or more of A, B or C" should be understood to mean only A, only B, only C or combinations of A and B, A and C, B and C, and A, B, and C.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/− 0.1% of the stated value (or range of values), +/− 1% of the stated value (or range of values), +/− 2% of the stated value (or range of values), +/− 5% of the stated value (or range of values), +/− 10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

What is claimed is:

1. A picker head comprising:
    a tip comprising
       a first end;
       a second end comprising an opening; and
       a bore extending from the first end to the opening;
    a piston comprising a first end and a second end, wherein the second end is configured to be inserted into the bore; and
    a sealing fluid configured to at least partially fill the bore, wherein when the sealing fluid is within the bore the sealing fluid comprises a first side proximal to the first end of the tip and a second side proximal to the opening,
    wherein the sealing fluid is selected to satisfy the condition given by:

$F_{DSF} > F_{DBS}$ wherein $F_{DSF}$ represents a force required to displace the sealing fluid within the bore; and wherein $F_{DBS}$ represents a force required to displace a fluid or material within a portion of the bore extending from the second side of the sealing fluid to an external side of the opening.

2. The picker head of claim 1, wherein the force to displace the sealing fluid is a function of one or more of (1) at least one of the viscosity or surface tension of the sealing fluid; (2) a gap distance between an outer wall of the piston and an inner wall of the tip; (3) friction force of the outer wall of the piston; (4) friction force of the inner wall of the tip; or (5) a length of a portion of the bore extending from the first side of the sealing fluid to the second end of the tip.

3. The picker head of claim 1, wherein the sealing fluid is a liquid.

4. The picker head of claim 3, wherein the sealing fluid has a viscosity of approximately 0.2-80,000 mPa-s.

5. The picker head of claim 1, further comprising a hydraulic fluid at least partially filling a portion of the bore between the second side of the sealing fluid and the opening.

6. The picker head of claim 5, wherein at least one internal section of the bore is coated with a substance that attracts the hydraulic fluid.

7. The picker head of claim 1, wherein at least one section of the piston is coated with a substance to repel the sealing fluid.

8. The picker of claim 5, wherein the sealing fluid and the hydraulic fluid are different liquids.

9. The picker of claim 5, wherein the sealing fluid and the hydraulic fluid are immiscible with each other.

10. The picker head of claim 1, further comprising a gap between an inner wall of the tip and an outer wall of the piston having a clearance of approximately 0.01-100 μm.

11. The picker head of claim 1, wherein the sealing fluid is further selected to satisfy the condition given by:

$$\Delta V_{sealing\ fluid} + \Delta V_{piston} \Delta V_{bore\ segment} = 0$$

wherein $\Delta V_{sealing\ fluid}$ represents a change in volume of the sealing fluid within a pre-determined portion of the picker head when the piston is moved from a first state to a second state; wherein $\Delta V_{piston}$ represents a change in volume of the piston within the pre-determined portion of the picker head when the piston is moved from the first state to the second state; and wherein $\Delta V_{bore\ segment}$ represents a change in volume of a bore segment comprising any portion of the bore and the opening within the pre-determined portion of the picker head not occupied by the sealing fluid or the piston when the piston is moved from the first state to the second state.

12. The picker head of claim 1, wherein the opening has a first diameter, wherein the piston has a second diameter, and wherein the ratio of the second diameter to the first diameter is greater than 1:1.

13. The picker head of claim 12, wherein the ratio is greater than 1:1 and less than 2:1.

14. The picker head of claim 12, wherein the ratio is at least 1.9:1.

15. The picker head of claim 12, wherein the ratio is at least 1.5:1.

16. The picker head of claim 12, wherein the first diameter is 250 μm.

17. The picker head of claim 16, wherein the second diameter is greater than 250 μm.

18. A picker comprising:
a picker head comprising
a tip comprising
a first end;
a second end comprising an opening;
a bore extending from the first end to the opening;
a piston comprising a first end and a second end, wherein the second end is configured to be inserted into the bore; and
a sealing fluid configured to at least partially fill the bore, wherein when the sealing fluid is within the bore the sealing fluid comprises a first side proximal to the first end of the tip and a second side proximal to the opening,
wherein the sealing fluid is selected to satisfy the condition given by:

$$F_{DSF} > F_{DBS}$$

wherein $F_{DSF}$ represents a force required to displace the sealing fluid within the bore; and wherein $F_{DBS}$ represents a force required to displace a fluid or material within a portion of the bore extending from the second side of the sealing fluid to an external side of the opening.

19. The picker of claim 18, further comprising:
a driver; and
a gripper mating the driver to the piston.

20. The picker of claim 19, further comprising a mount connecting the driver, the gripper, and the picker head to an imaging or detection device.

* * * * *